United States Patent [19]
Gutierrez et al.

[11] Patent Number: 5,871,720
[45] Date of Patent: Feb. 16, 1999

[54] COSMETIC COMPOSITIONS WITH DBS AND FUNCTIONALIZED SILICONES

[75] Inventors: Adriana Urrutia Gutierrez, Westfield; Joseph James Albanese; Robert Joseph Bianchini, both of Belle Mead; Steven Louis Fantano, Hackettstown, all of N.J.

[73] Assignee: Colgate-Palmolive Company, New York, N.Y.

[21] Appl. No.: 974,946

[22] Filed: Nov. 20, 1997

[51] Int. Cl.$^6$ .................................................. A61K 7/00
[52] U.S. Cl. .................................. 424/65; 424/66; 424/68; 424/401
[58] Field of Search .................................. 424/59, 65, 66, 424/68, 401

[56] References Cited

U.S. PATENT DOCUMENTS

| | | | |
|---|---|---|---|
| 3,441,537 | 4/1969 | Lengnick | 260/46.5 |
| 4,346,097 | 8/1982 | Schweiss et al. | 424/273 |
| 4,440,742 | 4/1984 | Marscher | 424/65 |
| 4,518,582 | 5/1985 | Schamper et al. | 424/66 |
| 4,719,102 | 1/1988 | Randhawa et al. | 424/66 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,816,261 | 3/1989 | Luebbe et al. | 424/65 |
| 4,822,602 | 4/1989 | Sabatelli | 424/65 |
| 4,863,721 | 9/1989 | Beck et al. | 424/47 |
| 5,302,382 | 4/1994 | Kasprzak | 424/78.3 |
| 5,405,605 | 4/1995 | Shin | 424/68 |
| 5,449,519 | 9/1995 | Wolf et al. | 424/401 |
| 5,490,979 | 2/1996 | Kasat et al. | 424/66 |
| 5,500,209 | 3/1996 | Ross et al. | 424/66 |
| 5,531,986 | 7/1996 | Shevade et al. | 424/68 |
| 5,603,925 | 2/1997 | Ross et al. | 424/65 |
| 5,609,855 | 3/1997 | Oh et al. | 424/65 |

FOREIGN PATENT DOCUMENTS

| | | |
|---|---|---|
| 0 260 030 A2 | 3/1988 | European Pat. Off. . |
| 0 291 334 A2 | 11/1988 | European Pat. Off. . |
| 0 451 002 A2 | 3/1991 | European Pat. Off. . |
| 0 512 770 A1 | 11/1992 | European Pat. Off. . |
| WO 92/19221 | 11/1992 | European Pat. Off. . |
| WO 96/26709 | 9/1996 | European Pat. Off. . |
| 2 280 111 A | 7/1994 | United Kingdom . |

OTHER PUBLICATIONS

A. Zombeck, "Novel Formulations Bawsed on Nonaqueous Emulsions of Polyols in Silciones", 22–25 Oct. 1996, pp. 1–12.

Walter Noll, "Chemistry and Technology of Silicones", 1968 by Academic Press Inc., pp. 190–196 and 239–245.

*Primary Examiner*—José G. Dees
*Assistant Examiner*—Michael A. Williamson
*Attorney, Agent, or Firm*—Rosemary M. Miano

[57] ABSTRACT

The invention comprises a cosmetic composition which is a translucent to clear stick having low tack. The cosmetic sticks are formed by combining (a) from 5.0–50.0 weight percent of a silicone fluid phase which comprises at least one hydroxy functionalized silicone fluid, at least one stabilizing agent and, optionally at least one additional silicone material; (b) from 40–95 weight percent of a gellant/solvent phase which comprises a mixture of dibenzylidene sorbitol and at least one solvent such as a polyhydric alcohol (for example, propylene glycol); and (c) an effective amount of at least one active ingredient.

33 Claims, 1 Drawing Sheet

COSMETIC COMPOSITIONS WITH DBS AND FUNCTIONALIZED SILICONES

FIELD OF THE INVENTION

This invention relates to cosmetic compositions in the form of solid sticks which are based on using dibenzylidene sorbitol as a gellant for sticks, especially propylene glycol based sticks, in combination with a functionalized silicone fluid whereby a significant reduction in tackiness is provided. The cosmetic compositions of the invention may be used to formulate deodorant and/or antiperspirant sticks, especially those which are translucent to clear in appearance.

BACKGROUND OF THE INVENTION

Dibenzylidene sorbitol (also called dibenzaldehyde monosorbitol acetal, or dibenzyl monosorbitol acetal or dibenzylidene monosorbitol acetal) and derivatives thereof such as those which are substituted on one or both of the aromatic rings with a fluorine or methoxy group and those which have the sorbitol portion replaced with other reduced sugars such as xylitol or ribitol as described in U.S. Pat. No. 5,609,855 assigned to Procter & Gamble (collectively referred to as dibenzylidene sorbitol or "DBS") may be used in various food and cosmetic applications. For cosmetic uses the more interesting ones are those focused on obtaining a translucent or clear product. While dibenzylidene sorbitol is stable in alkaline or neutral media, such compounds are not stable in acidic media. In an acidic environment, such as in the presence of acidic antiperspirant materials, and when in the presence of even small amounts of water, the dibenzylidene sorbitol deteriorates and breaks down. Also, the use of DBS sometimes causes problems in the aesthetics of cosmetic products or problems with structural properties. Accordingly, there is a need to find a way to form products containing DBS which are stable and which have acceptable aesthetics.

The use of DBS requires the use of polyhydric alcohols such as propylene glycol as a solvent if a clear, transparent product is desired. The high propylene glycol content, when combined with aluminum salts which are included in antiperspirant compositions for wetness control, contribute to undesirable tackiness or a sticky feel for these products when applied to the axilla region of the body. DBS clear antiperspirant sticks were first formulated in the late 1970's. There have been continued technical efforts to reduce the negative sensory attributes. Some of these efforts have focused on alternative solvents to replace a portion of the propylene glycol with organic esters known in the art as emollients. This creates a further problem since many of these emollients are either unsafe for personal care products or do not achieve acceptable aesthetics.

For formulating personal care products the incorporation of silicone fluids is known in the art. Silicone fluids such as cyclosiloxanes (for example, DOW CORNING® 244 and 245 Fluids) are used in some major commercial products. Silicone fluids are used because of their low tackiness, superior glide and skin-feel properties. However, silicone fluids are difficult to introduce into DBS based cosmetic stick products such as antiperspirants because they are not good solvents for DBS and they are not readily compatible with propylene glycol and many organic esters or emollients.

Sonic of the efforts on each of these fronts are described as follows. For example, some efforts have focused on the stability of DBS. United Kingdom Patent GB 2 280 111 assigned to Union Camp Corporation, describes a gel stick composition comprising a dihydric alcohol as a primary solvent, a co-solvent such as low molecular weight polyethylene glycol, water and/or glycerine, a buffering agent and DBS as a gelling agent.

U.S. Pat. No. 4,720,381 to Schamper et al notes stability problems with this approach and itself describes the use of solvents having less reactive hydroxy groups or alcohols with selected chain lengths in a DBS composition.

U.S. Pat. No. 4,816,261 to Luebbe et al describes stable deodorant gel stick compositions comprising DBS with a polar solvent and a coupling agent such as polypropylene glycol ethers of fatty alcohols.

U.S. Pat. No. 4,822,602 to Sabatelli teaches the use of dimethicone copolyols and volatile silicones in clear DBS-based sticks.

PCT publication WO 96/26709 assigned to Gillette describes clear DBS-based antiperspirant sticks with hydroxypropyl cellulose, dimethicone copolyol and EDTA.

U.S. Pat. No. 5,405,605 to Shin teaches anhydrous clear antiperspirant sticks substantially free of lower monohydroxy alcohols and which contain dibenzilidene monosorbitol with weak basic organic nitrogen containing compounds as a stabilizing agent.

U.S. Pat. No. 4,518,582 to Schamper, et al discloses an antiperspirant stick composition containing dibenzyl monosorbitol acetal in the presence of acidic antiperspirant-active salts, which composition is stable for extended periods of time at elevated temperatures. The composition contains at least a reactive solvent (such as water, methanol, ethanol, n-propanol, ethylene glycol, 1,2-propylene glycol, 1,3-propylene glycol, etc.), dibenzyl monosorbitol acetal, an antiperspirant-active compound, and a gel stabilizer such as magnesium sulfate, zinc acetate and mixtures thereof. This patent discloses that the stabilizer prevents or retards deterioration of the gelled sticks, especially when exposed to elevated temperatures.

Another patent disclosing stabilizers for solid gel antiperspirant sticks containing an acidic antiperspirant-active compound in the presence of dibenzyl monosorbitol acetal is U.S. Pat. No. 4,719,102 to Randhawa, et al. This patent discloses that the sticks include a solvent which is a small, polar organic compound such as cyclic esters, amides, amines, ketones, ureas, carbamates, sulfoxides and sulfones, and their open chain analogs; a cosolvent such as primary or low molecular weight alcohols and/or glycols; dibenzyl monosorbitol acetal; an antiperspirant-active compound; and a gel stabilizer such as N-(2-hydroxyethyl) fatty ($C_8$–$C_{20}$) acid amides, magnesium sulfate, zinc acetate, acetamide monoethanol amine and hexamethylenetetramine, and mixtures thereof.

U.S. Pat. No. 4,722,835 to Schamper, et al also discloses antiperspirant gel stick compositions gelled with dibenzyl monosorbitol acetal and containing an acidic antiperspirant compound, and also containing a stabilizer for the gel. This patent teaches that the compositions include a solvent which is a small, polar organic compound, as discussed previously in connection with U.S. Pat. No. 4,719,102; dibenzyl monosorbitol acetal; an antiperspirant-active compound; and a gel stabilizer such as zinc oxide, calcium acetate, magnesium oxide, calcium carbonate, calcium hydroxide, magnesium carbonate, sodium carbonate, zinc carbonate and potassium carbonate. This patent discloses that these basic metallic salt gel stabilizers can stabilize the gel, even at high temperatures.

U.S. Pat. No. 5,490,979 to Kasat et al describes a clear DBS stick comprising guanidine carbonate as the buffer and which is made by a unique processing method.

Other patent documents also disclose antiperspirant sticks gelled with a dibenzylidene sorbitol and include stabilizers for the gel.

EP Application No. 451,002 A2 discloses a stable, substantially anhydrous and substantially lower monohydric alcohol free, transparent, gelled, antiperspirant composition gelled by dibenzylidene monosorbitol acetal, containing acidic antiperspirants, and utilizing dihydric alcohols containing 3 to 6 carbon atoms as solvents, with the acetal being stabilized against hydrolysis and the formation of benzaldehyde by the presence of a stabilizing amount of a selected organic base, the organic base being a weakly basic, nitrogen-containing, organic compound.

EP Application No. 512,770 A1 discloses a stable, substantially anhydrous and substantially lower aliphatic monohydroxy alcohol free cosmetic composition gelled by dibenzylidene monosorbitol acetal, and containing acidic antiperspirant compounds and utilizing dihydroxy aliphatic alcohols containing 3–6 carbon atoms as solvents, wherein the dibenzylidene monosorbitol acetal gelling agent is stabilized against hydrolysis and the formation of benzaldehyde by the presence of a stabilizing amount of a selected inorganic base, the inorganic base including alkali and alkaline earth metal oxides, hydroxides, carbonates or bicarbonates, and trivalent metallic hydroxides.

PCT No. WO92/19221 discloses solid antiperspirant compositions in gel stick form, having an acid pH, and including (1) an antiperspirant active; (2) a gelling agent selected from the group consisting of substituted and unsubstituted dibenzylidene alditols; (3) a solvent for the gelling agent, preferably including a solvent material selected from the group consisting of monohydric and polyhydric alcohols, and mixtures thereof; and (4) a gelling agent stabilizer, the stabilizer being a basic metallic salt of an acid having a pKa of from about 3.8 to about 6.5 at 25 degrees C., the salt being at least partially soluble in the composition and being selected from the group consisting of $C_4$–$C_6$ dicarboxylate salts, $C_6$–$C_8$ monocarboxylate salts, and substituted or unsubstituted benzoate salts, and mixtures thereof, the gelling agent stabilizer not containing amino or amido functionalities. This patent document teaches that for clear or translucent sticks, the gelling agent stabilizer present in the composition should be fully soluble in the composition, in order to minimize refraction of light.

The foregoing patent documents also disclose methods for forming the disclosed antiperspirant stick compositions containing the antiperspirant materials and gelling agent. In particular, attention is directed to U.S. Pat. Nos. 4,719,102 and 4,722,835. Each of these patents discloses processes of forming the stick compositions, including dissolving the antiperspirant active in one phase and the dibenzyl monosorbitol acetal gellant in another phase. The two phases are then combined and poured into a mold or into the final package. The other components are added to either of the two phases depending on the compatibility of the component with the phases. More phases can be utilized, if desired, by forming a separate solution of some of the components, with the separate phases then being added to either of the two main phases; or all of the phases could be poured together at the end, as, for example, with a multi-stream filling head or an in-line mixer.

PCT No. WO92/19221 discloses a process of forming an antiperspirant gel stick, including preparing a solution containing the gelling agent, a solvent for the gelling agent, and the gelling agent stabilizer; mixing an antiperspirant active into such solution; and cooling the solution to form a gel.

There have also been efforts to develop DBS compositions to improve the aesthetics and/or mechanical properties while not sacrificing stability.

U.S. Pat. No. 4,346,097 to Roehl discloses a solid translucent gelled antiperspirant composition comprising DBS with an oleaginous compound (such as selected siloxanes, selected esters with an aliphatic character and branched chain hydrocarbons) to reduce stickiness.

PCT Publication Number 96/26709 to Vu et al describes a clear gel cosmetic stick which includes a liquid vehicle, an antiperspirant salt dissolved in the liquid vehicle, DBS and one or both of hydroxypropyl cellulose and a chelating agent. The hydroxypropyl cellulose maintains the hardness of the stick.

U.S. Pat. No. 4, 863,72 1 to Beck et al describes the use of particulate cellulose ether polymers such as hydroxyethyl cellulose in antiperspirant compositions which are substantially free of polar solvents.

European Patent 0 260 030 B1 assigned to Unilever N.V. describes a transparent deodorant stick containing DBS and a thickening agent such as a chemically modified cellulose, polyacrylic acid, and/or polyacrylic acid copolymers and mixtures of the foregoing.

Other references of interest include U.S. Pat. No. 4,472, 835 to Schamper et al; Zombeck, A., "Novel Formulations Based on Nonaqueous Emulsions of Polyols in Silicones" (Paper presented at the 19th IFSCC Congress, Sydney, Oct. 22–25, 1996); and Schamper, T., et al, "Acid Stable Dibenzylidene Sorbitol Gelled Clear Antiperspirant Systems", *J. Soc. Cosmet. Chem.*, Vol. 37, pages 225–231 (July/August 1986); Smith, J. M., et al, J. Mater. Chem., 5(11): 1899–1903 (1995).

There continue to be efforts to formulate improved cosmetic compositions especially sticks which have translucent to clear appearance and which have aesthetically acceptable properties. U.S. Pat. No. 5,500,209 to Ross et al describes a gel or stick composition for reduction of body malodor using a polyamide gelling agent. This composition is stated to have good stability and to be able to provide a clear antiperspirant or deodorant product with good structural integrity.

U.S. Pat. No. 5,603,925 to Ross et al teaches the use of a polyamide gelling agent in an antiperspirant product. The composition uses a glycol-free solvent system to reduce the problems of tack and achieve more acceptable properties.

U.S. Pat. No. 4,440,742 to Marchner discloses a stable cosmetic stick deodorant without the use of bacteriostats and comprising a polyhydric alcohol (such as propylene glycol) solidified by a fatty acid soap and containing from 0.1–70% alkali metal bicarbonate.

U.S. Pat. No. 4,822,602 to Sabatelli describes cosmetic compositions such as deodorant and antiperspirant sticks comprising (a) water-soluble active; (b) dimethicone copolyol; (c) volatile silicone oil; (d) propylene glycol; (e) C2–C4 monohydric alcohol; (f) water; (g) solidifying agent (such as soap type gel forming agents and DBS); and (h) coupling agent (such as C6–C22 fatty alcohols and propylene glycol ethers of C4–C22 fatty alcohols).

U.S. Pat. No. 4,725,430 teaches a clear or translucent cosmetic stick containing an acidic material (such as antiperspirant salts) and a reactive solvent (for example, various propylene glycols) using DBS as the gelling agent and an N-(2-hydroxyethyl) acetamide as the stabilizing agent.

U.S. Pat. No. 5,302,382 to Kasprzak describes a method of making stable emulsified personal care products which includes the steps of (i) forming an anhydrous silicone mixture having a silicone oil or silicone gum with two silicone oxyalkylene copolymers; (ii) forming an aqueous based pre-emulsified personal care product; and (iii) adding the anhydrous silicone mixture directly to the pre-emulsified personal care product without further emulsification.

U.S. Pat. No. 5,449,519 to Wolf et al describes a cosmetically acceptable composition with keratolytic activity which composition includes a carrier molecule having at least one hydroxyl or amino group.

U.S. Pat. No. 5,531,986 to Shevade et al describes a low residue antiperspirant solid stick containing an antiperspirant active, volatile and nonvolatile silicone materials, dimethicone copolyol and high-melting point and low-melting point waxes.

There still remains a need, however, to develop translucent, preferably clear, cosmetic products which provide reduced tack in a DBS product. Thus, it is an object of the present invention to provide a cosmetic composition which comprises DBS and which provides reduced tack when applied to the skin. It is a further object of the invention to provide cosmetic compositions containing DBS which can be used to form deodorant and/or antiperspirants which are translucent to clear. It is yet another object of the invention to provide cosmetic compositions which enhance the compatibility of DBS in propylene glycol systems which also contain silicone fluids. These and other objects of the invention will be apparent from the following description of the invention.

SUMMARY OF THE INVENTION

The invention comprises a cosmetic composition which is a translucent to clear stick having low tack. The cosmetic sticks are formed by combining the components described below to form a two phase system. These components, in weight percent based on the total weight of the composition, are:

(a) from 5.0–50.0 weight percent of a silicone fluid phase (as the first or internal phase) which comprises at least one hydroxy functionalized silicone fluid, at least one stabilizing agent and, optionally at least one additional silicone material;

(b) from 40–95 weight percent of a gellant/solvent phase (as the second or external phase) which comprises a mixture of dibenzylidene sorbitol and at least one solvent such as a polyhydric alcohol (for example, propylene glycol);

(c) an effective amount of at least one active ingredient; and (d) optionally one or more members selected from the group consisting of emollients, fragrances, coloring agents, etc., wherein the materials listed in parts (c) and (d) may become part of either of the phases described in part (a) or part (b).

DETAILED DESCRIPTION OF THE INVENTION

Figure 1:
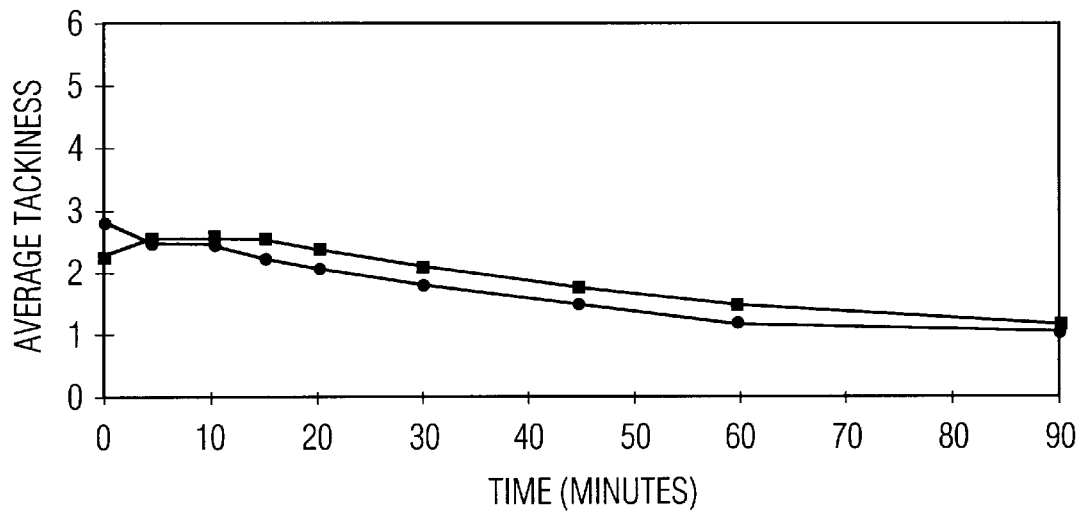
FIG. 1 shows data from a Forearm Flex Test done with an antiperspirant sample from Example 5 formulated with DBS and silanol (line with circles) and a commercial deodorant product formulated with DBS but without silanol (line with squares). The tack profile shows that the formulation of Example 5 is 5–10% less tacky than a commercial deodorant stick which contains no antiperspirant. This is significant because the addition of an antiperspirant salt creates increased problems with tack. The ability of an antiperspirant formulation to perform as well or better than a deodorant stick which does not contain an antiperspirant salt is a significant development.
Figure 2:
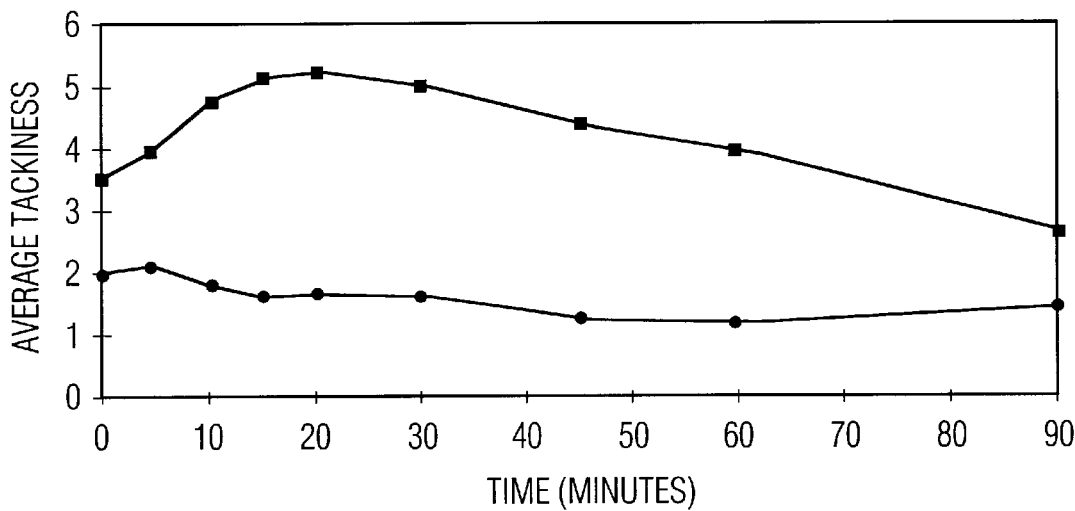
FIG. 2 shows data from a Forearm Flex Test done with an antiperspirant sample from Example 5 formulated with DBS and silanol (line with circles) as compared to a clear, commercially available antiperspirant stick formulated with DBS but without silanol (line with squares). The tack profile of the formulation of Example 5 is significantly less tacky (on the order of 65–70% less) than the commercial product. This result demonstrates the superiority of the present invention.

The compositions of this invention are made by combining the components described above in a two phase system to form a stick cosmetic composition. The first phase is the silicone fluid phase and comprises at least one hydroxy functionalized silicone fluid and at least one stabilizing agent. Compounds of Formula I are described as follows and can be used with or without additional silicone fluids. Suitable functionalized silicone fluids are hydroxy functional fluids with the general structure of Formula I:

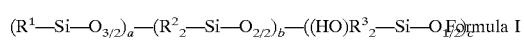

$$(R^1\text{—Si—}O_{3/2})_a\text{—}(R^2{}_2\text{—Si—}O_{2/2})_b\text{—}((HO)R^3{}_2\text{—Si—}O_{1/2})_c \quad \text{Formula I}$$

where each of $R^1$, $R^2$, and $R^3$, may be alike or different and are each independently selected from the group consisting of C1–C4 straight chain alkyls (especially methyl); a is a number in the range of 0–10, with particular values of "a" being 0 for linear compounds and 1–10 for branched compounds (for example 6–8); b is a number in the range of 0–10,000, with particular values of "b" being 4–6000; c is a number in the range of 1–10, with particular values of "c" being 2 when the compound is linear and at least 3 when there is branching; provided that a and b cannot both equal zero at the same time. It is to be recognized that a, b, and c are average values (including whole numbers and fractions) and mixtures of compounds with various values for a, b, c, $R^1$, $R^2$, and $R^3$ may also be used.

Examples of compounds of Formula I include:

(a) linear polydimethylsiloxanediols where a=0, b=4–6,000 (for example, an average value of 4, 40 or 6,000);

(b) linear polydimethylsiloxanediols where a=0, b=4–1,000, and c=2;

(c) multifunctional branched siloxanes where a=1–2, b=0–1,000, and c=3–4;

(d) linear polydimethylsiloxanediols where a=0, b=40 and c=2;

(e) multifunctional branched siloxanes where a=1, b=16, and c=3;

(f) multifunctional branched siloxanes where a=1–2, b=10–1,000, and c=3–4;

(g) mixtures of the particular compounds described in parts (a)–(f), for example, mixtures wherein the average structure of the mixture is described by a=0.1, b=4–6,000, and c=2–7; and (h) two component mixtures of the particular compounds described in parts (a)–(f) wherein one component is 0.1–99% of the composition and the other component is the remainder to 100%.

For each of the groups listed as (a)–(f) above, particular examples of the compounds are when each of the R groups is selected to be methyl. Also, for any of the groups (a)–(g), additional silicone fluids such as dimethicone may be added, for example in amounts of 0.1–90% functionalized silicone and 10–99.9% silicone fluid or fluids.

One particular group of compounds of Formula I are linear silanols of Formula IA, especially when b=40:

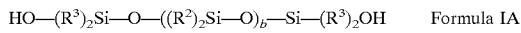
$$HO-(R^3)_2Si-O-((R^2)_2Si-O)_b-Si-(R^3)_2OH \qquad \text{Formula IA}$$

Some of the compounds of Formula I may be purchased commercially. For methods of making other compounds of this invention descriptions of suitable methods may be found in the literature for example, U.S. Pat. No. 5,302,382 to Dow Corning; U.S. Pat. No. 3,441,537 to Stauffer Chemical Company; and Noll, W., *Chemistry and Technology of Silicones*, (Academic Press, Inc. Orlando, Fla. 1968) especially at pages 190–196 and 239–245, all of which are incorporated herein by reference.

While the hydroxy functionalized silicones described above are preferably selected to have a viscosity that does not require additional silicone materials (for example, having a viscosity in the range of up to 60,000 centistoke (cst), it is possible to use compositions which are a blend of hydroxy functionalized silicones having a high viscosities such as those having a high viscosity (>500,000 centistoke) dimethiconol in dimethicone where the dimethicone has a viscosity in the range of 5–350 centistoke (for example, DOW CORNING® 1403 Fluid).

For high viscosity functionalized silicones (for example, the silicone gums), and for the purpose of facilitating its handling and processing, these materials are generally provided as blends with another volatile or non-volatile low viscosity silicone such as CYCLOMETHICONE, or a non-volatile linear silicone fluid having a viscosity of about 5 to 350 centistoke. Such dimethyl silicone polymers terminated with hydroxyl groups have been assigned the INCI name "DIMETHICONOL" by The Cosmetics, Toiletries and Fragrance Association, Inc., Washington, D.C. (CTFA). Blends of such silicone gums with a volatile low viscosity cyclic silicone have been assigned the INCI name "CYCLOMETHICONE (and) DIMETHICONOL" by the CTFA. Other blends of such silicone gums with a non-volatile low viscosity linear silicone have been assigned the INCI name "DIMETHICONE (and) DIMETHICONOL" by the CTFA. The DIMETHICONOL content of such blends is typically in the range of about 12 to 14 percent by weight, and the blend viscosity may range from 500 to about 20,000 centistoke, generally in the range ol about 4,000 to 5,000 centistoke.

Other volatile low viscosity methylsilicone fluids are described in U.S. Pat. No. 5,302,382 to Kasprzak, incorporated by reference herein. Examples of methylsilicone fluids having viscosities of less than about one hundred centistoke measured at twenty-five degrees Centigrade, preferably less than about five centistoke and also methylsilicone fluids having a viscosity in the range of 1–350 centistoke are disclosed.

One group of methylsilicone fluids is volatile low viscosity methylsilicone fluid containing dimethylsiloxane units and, optionally, trimethylsiloxane units. Representative compounds are cyclopolysiloxanes of the formula $[(CH_3)_2SiO]_x$, and linear short chain siloxane compounds of the formula $(CH_3)_3SiO[(CH_3)_2SiO]_ySi(CH_3)_3$, in which x is an integer having a value of from three to ten,(especially 4–6) and y is an integer having a value of from zero to about four. The cyclopolysiloxanes have been assigned the INCI name "CYCLOMETHICONE" by The Cosmetics, Toiletries and Fragrance Association, Inc., Washington, D.C. (CTFA).

The silicone fluid phase can also, optionally, include other silicone materials even when the purpose is for reasons other than viscosity modification. Particular silicone fluids are selected so that a stable silicone/glycol suspension is formed when the two phases are combined and mixed. Such materials can include, for example, other silicone fluids such as polydimethylsiloxanes, polydiethylsiloxanes, and polymethylethylsiloxanes, having a viscosity in excess of 350 centistoke and up to 2,500,000 centistoke, preferably, 350–10,000 centistoke. Further examples include cetyl dimethicone copolyol, dimethicone copolyol (such as DOW CORNING® 2501, Q2-5220 and 5324 products); a mixture of cyclomethicone and dimethiconol (such as DOW CORNING® 1401 product); a mixture of dimethicone and dimethiconol (such as DOW CORNING® 1403 product); cetyl dimethicone (DOW CORNING® 2502 product); and stearyl dimethicone (DOW CORNING® 2503 product).

A stabilizing agent is also included in the silicone phase. This stabilizing agent may be selected from several types of groups. One such group is silicone polyether surfactants having a hydrophilic/lipophilic balance ("HLB" value) compatible with the solvent and the silicone phase particularly to form a stick composition. For example, if propylene glycol is used as the solvent a polyether surfactant with an HLB value of 1–10 is preferred (for example, DOW CORNING® 3225 C Formulation Aid (HLB=1.7) DOW CORNING® 190 Surfactant (HLB=5)). If tri- and/or tetrapropylene glycol is used as the solvent a polyether surfactant with an HLB value in the range of 5–10 is preferred. For example, a cosmetic composition may be formed wherein the stabilizing agent is a member of the group consisting of silicone polyether surfactants having a hydrophilic/lipophilic in the range of 1–10, and the solvent comprises greater than 50% by weight of propylene glycol, dipropylene glycol, tripropylene glycol or tetrapropylene glycol.

A particular siloxane polyether has the following Formula II:

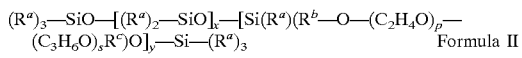
$$(R^a)_3-SiO-[(R^a)_2-SiO]_x-[Si(R^a)(R^b-O-(C_2H_4O)_p-\\(C_3H_6O)_sR^c)O]_y-Si-(R^a)_3 \qquad \text{Formula II}$$

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment $-(C_2H_4O)_p-(C_3H_6O)_s-$ has a molecular weight in the range of 200 to 5,000; the segment preferably having fifty to one hundred mole percent of oxyethylene units $-(C_2H_4O)_p-$ and one to fifty mole percent of oxypropylene units $-(C_3H_6O)_s-$; x has a value of 8 to 400; and y has a value of 2 to 40. Preferably $R^a$ is a methyl group, $R^c$ is H; m is preferably three or four whereby the group $R^b$ is most preferably the radical $-(CH_2)_3-$; and the values of p and s are such as to provide a molecular weight of the oxyalkylene segment $-(C_2H_4O)_p-(C_3H_6O)_s-$ of between about 1,000 to 3,000. Most preferably p and s should each have a value of about 18 to 28.

A second siloxane polyether has the Formula III:

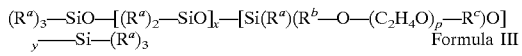
$$(R^a)_3-SiO-[(R^a)_2-SiO]_x-[Si(R^a)(R^b-O-(C_2H_4O)_p-R^c)O]_y-Si-(R^a)_3 \qquad \text{Formula III}$$

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, an ester group such as acyl, or an aryl group such as phenyl; m has a value of two to eight; p has a value of 6 to 16; x has a value of 6 to 100; and y has a value of 1 to 20.

It should be understood that in both Formulas II and III shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^a$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Mixtures of silicone polyethers can also be used. Such mixtures include components which themselves met the HLB criteria described above or which, in combination, meet the HLB criteria described above.

In one particular embodiment the silicone fluid phase comprises at least a portion of a silicone polyether surfactant to stabilize the cosmetic composition when it contains an antiperspirant active material. In antiperspirant compositions the polyether component is preferably used in an amount of 1.0–25.0 weight percent. These silicone polyethers can be added to the silicone fluid phase before the mixing of the first and second phases or the polyether can be added to the combined mixture at the end of the process during the cool down cycle. Examples of suitable silicone polyethers include DOW CORNING® 190 Surfactant (HLB of 5.6), DOW CORNING® 193 Surfactant (HLB of 12.–12.45), DOW CORNING® 2501 Cosmetic Wax (HLB of 19.0), DOW CORNING® 5200 (HLB of 6.83), DOW CORNING® 5324 (HLB of 5.0), DOW CORNING® 3225C Formulation Aid, and DOW CORNING® 5220 (HLB of 71.7).

The stabilizing agent can also be a high refractive index (greater than 1.4325) modifier, for example a member selected from the group consisting of isopropyl myristate, isopropyl palmitate, mineral oil, oleyl alcohol sorbitol, glycerol, octyl salicylate, octylmethoxycinnamate; phenyl siloxanes of Formula IV:

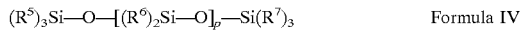

Formula IV where $R^5$, $R^6$ and $R^7$ are each independently selected from methyl and phenyl, and p is a number in the range of 0–10 (for example a trimethylphenylsiloxanes such as DOW CORNING® 556 Fluid; and polydiphenylsiloxanes, for example, tetramethyl tetraphenyl trisiloxane such as DOW CORNING® 704 Fluid and trimethyl pentaphenyl trisiloxane such as DOW CORNING® 705 Fluid).

Another stabilizing agent is a member selected from the group consisting of alkyl galactomannose (for example, N-Hance® AG 50 and N-Hance® AG 200 from Hercules Inc., Aqualon Division, Wilmington, Del.).

The second phase is the gellant/solvent phase. This phase is made by combining:

(a) 0.5–4.0 weight percent DBS (based on the total weight percent of the composition);

(b) 0.1–1.0 weight percent of a co-gellant or structural integrity enhancer selected from the group consisting of hydroxypropyl cellulose, alkyl ester thickeners (for example, PEG-150 pentaerythrityl tetrastearate called CROTHIX® from Croda Chemicals, Parsippany, N.J.), fumed silica (for example, Cab-O-Sil®, from Cabot, Flemington, N.J.; Aerosil® from DeGussa, Ridgefield Park, N.J.), waxes such as alkyl methylsiloxanes (for example, AMS-30 (C30–C45 alkyl methicone available from DOW CORNING CORPORATION, Midland, Mich.), selected guars such as an hydroxy $C_3$–$C_4$ alkyl guar having a level of hydroxyalkylation of 0.4–1.5 molar substitution as described in copending case filed on the same date herewith and incorporated herein by reference, entitled "Clear Antiperspirant Stick With Dibenzylidene Sorbitol and Guar and Process of Making Same" for which a serial number has not yet been received and referenced herein as Attorney Docket Number 5947. A particularly preferred combination is 0.05%–1.0% CROTHIX in combination with 1.0%–5.0% PPG-5 Cetoth-20 and a suitable base such as 0.1%–1.0% of guanidine carbonate. Hydroxypropyl cellulose may be used in an amount of 0.2%–1.0% by weight based on the total weight of the composition.

(c) 0.1–80 weight percent of a solvent selected from the group consisting of polyhydric alcohols for example, propylene glycol, dipropylene glycol, tripropylene glycol and tetrapropylene glycol, PPG-10 butane diol, 1.3-butane diol, PEG-6, PPG-425, including up to 50 percent of other solvents selected from propylene carbonate, diisopropyl sebacate, methyl pyrrolidone, and ethyl alcohol.

The third component used to make the compositions of the invention is at least one cosmetically active ingredient selected, for example, from the group consisting of antiperspirant salts, sunscreens, bacteriostats, fragrances and insect repellents.

Various antiperspirant active materials that can be utilized according to the present invention include conventional aluminum and aluminum/zirconium salts, as well as aluminum/zirconium salts complexed with a neutral amino acid such as glycine, as known in the art. See each of EP No. 512,770 A1 and PCT No. WO92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention. Suitable materials include (but are not limited to) aluminum chlorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO92/19221, the contents of which are incorporated by reference in their entirety herein.

The amount of antiperspirant active material incorporated in the stick composition of the present invention is, preferably, an antiperspirant effective amount; that is, an amount to reduce the flow of perspiration from the location (for example, axillary region of a human) to which the antiperspirant is applied. For deodorant products a level of from 0.5–2%,, more particularly 0.5–5.0% by weight based on the entire weight of the composition is used. For an antiperspirant product an amount of 5.0–25%,, particularly 5–20%, even more particularly 7–15%, and especially 7–12% by weight based on the total weight of the composition may be used. The amount of antiperspirant material utilized is dependent on the efficacy of the specific antiperspirant material, as well as a maximum amount which avoids a reduction in clarity of the final product.

For embodiments of the invention which contain an antiperspirant (either at a level denominated "deodorant" or at a level denominated "antiperspirant") it is preferred that a stabilizing agent also be included Examples of suitable stabilizing agents include cosmetically acceptable alkali metal salts, bases, amines and other nitrogen containing compounds, particularly guanidine carbonate (described in U.S. Pat. No. 5,490,979).

Examples of suitable sunscreens include octyl methoxycinnamate, aminobenzoic acid, octyl salicylate, oxybenzole and cosmetically acceptable ultraviolet light absorbers for example as listed in the *CTFA Cosmetic Ingredient Handbook* at page 98.

Suitable insect repelling agents include N,N-diethyl-m-toluamide ("DEET") and citronella.

Known bacteriostats include bacteriostatic quaternary ammonium compounds such as 2-amino-2-methyl-1-propanol (AMP), cetyl-trimethylammonium bromide, cetyl pyridinium chloride, 2,4,4'-trichloro-2'-hydroxydiphenylether (Triclosan), N-(4-chlorophenyl)-N'-(3,4-dichlorophenyl)urea (Triclocarban) and various zinc salts (for example, zinc ricinoleate). The bacteriostat can, illustratively, be included in the composition in an amount of 0.1–1.0% by weight, of the total weight of the composition. Triclosan, can illustratively be included in an amount of from 0.1% to about 0.5% by weight, of the total weight of the composition.

The fourth component used to make the compositions of the invention is the remainder and portion comprising one or more of the following optional ingredients: emollients, fragrances, coloring agents and ingredients having a lower refractive index than 1.4325 such as water, ethanol, wherein the materials listed in this fourth component may become part of either the silicone phase or the gellant/solvent phase.

Emollients may be selected from the group consisting of emollient oils such as a liquid mixture of hydrocarbons which are liquids at ambient temperatures (such as petroleum distillates and light mineral oils), mineral oil, peanut oil, sesame oil, avocado oil, coconut oil, cocoa butter, almond oil, saftflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate and lauryl lactate; fatty acids such as lauric, myristic, palmitic, stearic, oleic, linoleic, and behenic, acid; fatty alcohols such as lauryl, myristyl, cetyl, isocetyl, stearyl, isostearyl, oleyl, ricinoleyl, erucyl, and 2-octyl dodecanol, alcohols; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalene.

Any of the components such as the liquid esters and silicone fluids, materials characterized by their refractive indices, especially the silicone fluids, described above can be selected to enhance the clarity and transmission of light as evaluated by measurements of transmittance of light. One such device is a turbidimeter such as Model 965-10A Digital Direct-Reading Turbidimeter from Orbeco Analytical Systems, Inc., Farmingdale, N.Y., with the use of acceptable accepted test protocols such as ASTM D 5180-93 entitled "Standard Test Method for Quantitative Test for Turbidity in Clear Liquids; ASTM D1889-94 entitled "Standard Test Method for Turbidity of Water"; and selected methods from *Standard Methods for the Examination of Water and Wastewater* (American Public Health Association Washington D.C., 1995): No. 2130 "Turbidity". Values in the range of 30–950 nephelometric turbidity units (NTU), preferably below 800 NTU and more preferably below 200 NTU, and particularly below 100 NTU are preferred.

A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291 ,334 A2. Thus, according to the present invention, there are differences between transparent (clear), translucent and opaque compositions.

Particular embodiments of the invention which may be used are antiperspirant sticks having the following formulations which are at least translucent.

Because of the chemical instability of DBS in the presence of water in low pH media, it is preferred that antiperspirant formulations be essentially anhydrous and contain sufficient buffering agents to keep the pH in the range of 4.0–5.0. Deodorants and other cosmetic preparations which are at a higher pH do not require this restriction.

Particular compositions according to the present invention include those made by combining in percent by weight based on the total weight of the composition:
- (a) 6.0–35% of the silicone fluid phase;
- (b) 25–70% of a polyhydric alcohol selected from the group consisting of propylene glycol, dipropylene glycol, tripropylene glycol, tetrapropylene glycol and mixtures thereof;
- (c) 1.5–2.5% dibenzylidene sorbitol; and
- (d) 5–25% antiperspirant active.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

As noted above, the compositions of the present invention have less tack than conventional cosmetic sticks. This is especially true of antiperspirant sticks made according to the invention. Tack can be evaluated by various techniques including the Forearm Flex Test.

Forearm Flex Test

In this test the administrator first over-wraps the test products to hide their identity from the panelists and then gives each sample a code number to hide their identity from the statistician who will analyze the data. These precautions are done to avoid bias of the panelists and the test evaluators. Next, one of two products is applied to one arm at the crease of the elbow and the second product is applied to the same area of the other arm. The two products are applied in a similar manner. Product application is done by either counting the number of strokes or by weighing the products to be tested before and after. Products are applied in random fashion to eliminate left-handed or right-handed biases. The ambient room temperature and humidity are recorded. Using the same control product for every test allows for a comparison between test results for various experimental formulations. The panelists evaluate the tested products for several aesthetic attributes including, but not limited to, wetness, oily/greasy feel, glide, and, most importantly, tackiness/stickiness. The panelists evaluate initial tackiness immediately after a product application and repeatedly at predetermined time intervals for an overall time of 90 minutes. The assessment of tack is made by flexing the arm and judging the adherent forces between contacted skin surfaces. A scale of 1 to 7 is used by each panelist with 1=Not Tacky and 7=Extremely Tacky. The collected data is used to generate a "Tack Profile" which is a plot of Tackiness versus Time. Data analysis using a statistical software package called JMP from SAS Institute (Cary, N.C.) permits identification of products which are significantly different from the Control sample. The Control is selected to be a competitive benchmark currently in the marketplace which represents what is believed to be the best commercially available standard. In addition to an analysis of product performance at specific time periods, the performance of the tested sample throughout the 90 minute test period can be made by calculating the area under each curve in the Tack Profile graph and comparing the differences.

The following Examples are given as illustrative of the invention but other modifications may be made by those skilled in the art which are within the spirit and scope of the invention. Unless otherwise noted all amounts are in weight percents. All chemical symbols and scientific abbreviations have their usual and customary meanings and all temperatures are in degrees C. The aluminum zirconium tetrachlorhydrex glycine complex listed in the following examples is a solution comprising about 28% by weight actives in a mixture of polyhydric alcohols (such as Westchlor® ZR 35B from Westwood Chemical, Middletown, N.Y.). In addition about 0.75%±0.25 guanidine carbonate was added to the actives solution (although the amount may be varied from 0.5%–1.0% guanidine carbonate). It will also be appreciated by those skilled in the art that preheating of ingredients was done as needed to ensure good mixing.

EXAMPLES

Example A

General Method A

The general method used to make the compositions described in Examples 1–5 is as follows:
- (a) Weigh all of the ingredients to be combined in the silicone phase and place them in a 250 ml beaker. Heat the contents to 100 degrees C.
- (b) Weigh the aluminum zirconium tetrachlorhydrex gly and place it in a 50 ml beaker and heat it to a temperature of 100 degrees C.
- (c) Weigh the propylene glycol and place it in a 250 ml beaker.
- (d) Heat the beaker containing propylene glycol on a hot plate until the temperature of the contents is about 100 degrees C. while dissolving the cellulose in the propylene glycol. Continue heating this mixture until it is at a temperature of 130–135 degrees C.
- (e) Weigh the DBS, and add it to the mixture in Step (d) with stirring until the DBS is dissolved.
- (f) After the blend of propylene glycol/cellulose/DBS is clear and all the DBS has been dissolved, remove the solution from the hot plate and allow it to cool to a temperature of 110 degrees C.
- (g) Add the heated aluminum zirconium tetrachlorhydrex gly from Step (b) with stirring to the solution in Step (f) and immediately add the heated silicone mixture from Step (a) with very slow addition and with turbulent stirring to form the silicone/propylene glycol emulsion. The addition of the heated silicone mixture should be done at a slow rate. This addition should be done without continued heating to avoid degrading the DBS.
- (h) Pour the emulsion from Stop (g) into the desired container (mold, packaging, etc.) which is at a temperature in the range of the gelling point (100–105 degrees C.).

Example B

General Method B

Gel Phase

1) Charge the formula amount of Propylene Glycol (PG) to the main mixing vessel and begin agitation sufficient enough to create a vortex.

2) Slowly sprinkle-in the Hydroxypropyl Cellulose (HPC) or Hydroxypropyl Guar (HPG) into the PG.

3) Once the HPC or HPG is homogeneously dispersed begin heating to 60 degrees C. to facilitate complete hydration with continued agitation.

4) Slowly add Dibenzylidene Sorbitol (DBS) at 60 degrees C. Continue heating and mixing until 95–105 degrees C. Mix until all of the DBS is dissolved into solution.

Actives Phase

1) Add the actives to a suitable mixing vessel and heat to 95–105 degrees C. with agitation.

2) Charge to Gel Phase in the main mixing vessel once all of the DBS has been dissolved.

Silicone Phase

1) Charge the Dimethiconol to a suitable side mixing vessel and begin mixing.

2) Add the Phenyl Trimethicone and begin heating to 95C–105 degrees C.

3) Add the Dimethicone Copolyol and continue heating to 95C–105 degrees C.

4) Add to the combined Gel Phase/Actives Phase in the main mixing vessel.

Fragrance/Colors

1) Once combined Gel, Actives and Silicone Phases are homogeneous begin cooling to 10 degrees C. above the titer (gellation temperature).

2) Charge Fragrance/Colors with continued agitation.

3) Once Fragrance and Colors are incorporated begin filling into barrels at 5 degrees C. above the titer point.

Example C

Alternative Order of Addition

This method can be used when additional solvents partially replace propylene glycol or when the DBS level drops below 2 weight percent. Either of these occurrences lowers the dissolution temperature. Examples of such solvents with a lower DBS dissolution temperature include propylene carbonate, polyhydric alcohols (for example, dipropylene glycol, dipropylene glycol, tripropylene glycol, tetrapropylene glycol), PEG-6, carbonate, N-pyrrolidone and mixtures of such solvents.

Gel Phase

1) Charge the formula amount of Propylene Glycol (PG) to the main mixing vessel and begin agitation sufficient enough to create a vortex.

2) Slowly sprinkle-in the Hydroxypropyl Cellulose (HPC) or Hydroxypropyl Guar (HPG) into the PG.

3) Once the HPC or HPG is homogeneously dispersed begin heating to 60 degrees C. to facilitate complete hydration with continued agitation.

4) Slowly add Dibenzylidene Sorbitol (DBS) at 60 degrees C. Continue heating and mixing until 95–105 degrees C. Mix until all of the DBS is dissolved into solution.

Silicone Phase

1) Charge the Dimethiconol to a suitable side mixing vessel and begin mixing.

2) Add the Phenyl Trimethicone and begin heating to 95–105 degrees C.

3) Add the Dimethicone Copolyol and continue heating to 95–105 degrees C.

4) Add to the Gel Phase/Actives Phase in the main mixing vessel after all of the DBS has been dissolved.

Actives Phase

1) Charge the actives to a suitable mixing vessel and heat to 95–105 degrees C. with agitation.

2) Add the actives phase to the combined Gel Phase/Silicone Phase in the main mixing vessel.

Fragrance/Colors

1) Once the combined Gel, Actives and Silicone Phases are homogeneous begin cooling to 10 degrees C. above the titer (gellation temperature).

2) Added Fragrance/Colors with continued agitation. 3) Once Fragrance and Colors are incorporated begin filling into the desired package or mold at 5 degrees C. above the titer point.

Examples 1–4

Linear Silanols

The method of Example A was used with the amounts and types of ingredients as in Table 1. The amounts given are in weight percents based on the total weight of the composition as 100 percent.

TABLE 1

| Ex. | Silanol* | Surfactant DC 3225C | DC 556 Fluid | Propylene glycol | DBS | Hydroxy propyl cellulose | Al—Zr tetrachlor hydrex gly |
|---|---|---|---|---|---|---|---|
| 1 | 25.0 | 3.0 | 5.0 | 34.5 | 2.0 | 0.5 | 30.0 |
| 2 | 10.43 | 3.0 | 4.87 | 39.2 | 2.0 | 0.5 | 40.0 |
| 3 | 25.4 | 3.0 | 3.7 | 35.4 | 2.0 | 0.5 | 30.0 |
| 4** | 18.75 | 3.0 | 5.0 | 34.5 | 2.0 | 0.5 | 30.0 |

*The silanols used were linear silanols of the following formula: $HO(CH_3)_2SiO)_yH$. For Example 1, y = 4; for Examples 2 and 3, y = 40; and for Example 4, y = 6000.
**12.5% of Dimethicone 5 cst was added to 6.25% of the silanol for 18.75%.

The compositions of Examples 1–4 were evaluated by laboratory assessment and visual observation for selected properties. The results are listed in Table 2.

TABLE 2

| Example | Comments | Sensory Attributes |
|---|---|---|
| 1 | stable/soft/hazy | nontacky |
| 2 | stable/good structure/hazy | nontacky |
| 3 | stable/good structure | low tack |
| 4 | stable/no syneresis/excellent structure/hazy | small amount of tackiness |

Example 5

The method used to make Example 3 was repeated except that 2.5 weight percent of DBS was used, 1.0 weight percent of fragrance and 33.9 weight percent of propylene glycol was used. A sample made according to the method of Example 5 was evaluated using the Forearm Flex Test described above. This example uses a silicone surfactant and cyclomethicone. The results are shown in FIG. 1 and explained above.

Example 6

The method described in Example A was repeated except that a silicone polyether surfactant having a higher solids content was used instead of the dimethicone copolyol (and) cylcomethicone (DOW CORNING® 3225C Formulation Aid used in Examples 1–4). Such a material could also be made by taking the DC 3225C material and removing enough cyclomethicone to obtain a solids content of the surfactant of about 50% by weight of the surfactant. The branched silanol (hydroxy functional branched siloxane) used was a blend of linear and branched silanols wherein "a" had an average value of 0.1, "b" had an average value of 16 and "c" had an average value of 3.

The ingredient amounts were:

```
10.0% silanol
0.30% silicone polyether surfactant
51.7% propylene glycol
30.0% Al—Zr tetrachlorhydrex gly
2.0% DBS
1.0% hydroxypropyl cellulose
5.0% phenyltrimethicone (DOW CORNING ® 556 Fluid)

100% Total
```

This formulation showed more transparency than the formulations in Examples 1–4. The stick had very good structure and exhibited good gelling speed.

Example 7

The silanol in Examples 2 and 3 was formulated into a composition using the method described in Example A without surfactant and with the following ingredients:

```
28.8% silanol
3.7% phenyl trimethicone (DOW CORNING ® 556 Fluid)
35.0% propylene glycol
2.0% DBS
0.5% hydroxypropyl cellulose
30.0% Al—Zr tetrachlorhydrex gly

100%
```

The composition ol this example did not show acceptable stability and exhibited separation into two phases.

Example 8

The silanol in Examples 2 and 3 was formulated into a composition using the method described in Example A with the following ingredients:

```
25.8% silanol
3.0% dimethicone copolyol (and) cylcomethicone
(DOW CORNING ® 3225C
Formulation Aid)
3.8% phenyltrimethicone (DOW CORNING ® 556 Fluid)
34.9% propylene glycol
2.0% DBS
0.5% hydroxypropyl cellulose
30.0% Al—Zr tetrachlorhydrex gly

100%
```

After allowing the composition to stand overnight, it was examined and judged to be stable with good structure.

Examples 9–10

The silanol in Examples 2–3 was formulated into a composition using the method described in Example A except that a different surfactant was used. The amounts of the ingredients are listed in Table 3. All amounts are in weight percent based on the total composition as 100 percent.

TABLE 3

| Ex. | Sil-anol | Surfac-tant* | DC 556 Fluid | Propylene glycol | Hydroxy propyl cellulose | DBS | Al—Zr tetrachlor hydrex gly |
|---|---|---|---|---|---|---|---|
| 9 | 25.0 | 0.5 | 5.0 | 37.0 | 0.5 | 2.0 | 30.0 |
| 10 | 25.0 | 1.0 | 5.0 | 36.5 | 0.5 | 2.0 | 30.0 |

*Example 9 used a silicone polyether with an HLB of 5 (DC Surfactant 190) and Example 10 used a polyether surfactant with an HLB of 12.2 (DC Surfactant 193).

The compositions were evaluated as described in Example 8. The composition of Example 9 was judged to be stable with good structure. The formulation of Example 10 was judged to have poor stability after 24 hours and the silicone phase separated. Note that Example 10 with propylene glycol used a surfactant with an HLB value of 12.2 which is greater than 10.

Example 11

The method described in Example 8 was repeated with the following amounts of ingredients:

```
25.8% silanol
3.0% dimethicone copolyol (and) cylcomethicone
(DOW CORNING ® 3225C
Formulation Aid)
10.0% phenyltrimethicone (DOW CORNING ® 556 Fluid)
29% propylene glycol
2.0% DBS
0.2% hydroxypropyl cellulose
30.0% Al—Zr tetrachlorhydrex gly 100% Total
```

Using a scale of 0–10 where 0=opaque and 10=transparent, the composition was observed visually and rated as 4 for clarity.

Example 12

The silanol and polyether surfactant described in Example 6 were used with the method described in Example A for compositions formulated with the following amounts of ingredients:

```
10.0% silanol
0.30% polyether surfactant
15.0% phenyltrimethicone (DOW CORNING ® 556 Fluid)
41.7% propylene glycol
2.0% DBS
1.0% hydroxypropyl cellulose
30.0% Al—Zr tetrachlorhydrex gly

100%
```

The composition was evaluated using the scale described in Example 11 and rated as "9" indicating a clear composition.

Example 13

Propylene glycol (40.4%) and hydroxypropyl cellulose (1.0% KLUCEL) is charged to a main mixing vessel and heat is used to raise the temperature to about 100 degrees C. DBS (2.0%) is added and with stirring and heating until the DBS is melted into the solvent mixture (temperature is at 130–135 degrees C). Guanidine carbonate (0.3%) is added with cooling and stirring as the temperature is lowered to about 105–110 degrees C. In a separate container PPG-5-Ceteth-20 (5.0% PROCETYL AWS, from Croda) is added with stirring to the actives phase (30.0% of Al—Zr tetrachlorhydrex gly). A silicone phase is made in a separate vessel by combining silanol (10.0% of a silanol described in Example 6), a polyether surfactant of the type as described in Example 6 (0.03%), and phenyltrimethicone (10.0% of DOW CORNING® 556 Fluid) with heating and stirring to about 105 degrees C. The mixture with the actives is added at 105 degrees C. to the main vessel. Then the silicone phase is added. An emulsion is made with the combination of the contents of the two vessels with stirring and cooling to about 100 degrees C. Further cooling is allowed and when the mixture is at a temperature of about 85–90 degrees C, PEG-150 pentaerythrityl tetrastearate (1.0% CROTHIX) is added with stirring until melted. The mixture is allowed to cool as needed to a temperature in the range of 85–90 degrees C. and then may be poured into the final containers for setting. A composition made by such a process may be evaluated by the scale described in Example 11. It was soft but the combination helped to reduce droplet size of the internal phase, thus improving clarity.

Examples 14–18

The method of Example C was used with the amounts and types of ingredients listed in Table 5. The amounts given are in weight percents based on the total weight of the composition as 100 percent.

TABLE 5

| Ex. | Silanol* | Surfactant DC 3225 C | DC 556 Fluid | Propylene glycol | DBS | HPC*** or guar | Al—Zr tetrachlor hydrex gly |
|---|---|---|---|---|---|---|---|
| 14 | 17.5 | 2.1 | 2.7 | 45.6 | 1.75 | 0.35 | 30 |
| 15 | 17.5 | 2.1 | 2.7 | 30.6 PG** 5.0 PC 10.0 DPG | 1.75 | 0.35 | 30 |
| 16 | 20.3 | 3.0 | 3.7 | 40.9 | 1.75 | 0.35 | 30 |
| 17 | 20.3 | 3.0 | 3.7 | 40.75 | 1.75 | 0.50 | 30 |
| 18 | 25.4 | 3.0 | 3.7 | 34.65 | 1.75 | 0.50 | 30 |

*Silanols used were the type described in Examples 2 and 3.
**PG = propylene glycol; PC = propylene carbonate; DPG = dipropylene glycol.
***HPC = hydroxypropyl cellulose (KLUCEL MFF was used for Examples 14, 15 and 18. Guar (JAGUAR HP 120) was used for Examples 16 and 17. Note Example 18 also contained 1.0% fragrance.

Example 19

A composition may be made using Method B with the following amounts of ingredients: 41.5% propylene glycol, 1.75% DBS, 0.5% HPC, 30% Al Zr tetrchlorhydrex gly 20.3% silanol (of the type described in Examples 2 and 3), 2.5% phenyltrimethicone (DC 556), 2.1% surfactant (DC 3225C) and 1.25% fragrance. Preferably homogenization is used when adding the DBS and HPC.

Example 20

The method of Example 19 may be used with the following changes: 34.3% propylene glycol, 25.4% silanol, 3.7% phenyltrimethicone, and 3.0% surfactant.

Example 21

A composition may be made using Method B with the following amounts of ingredients: 41.5% propylene glycol, 1.5% DBS, 1.0% HPC, 30% Al Zr tetrchlorhydrex gly, 25.4% silanol (of the type described in Examples 2 and 3), 3.75% phenyltrimethicone (DC 556), 3.0% surfactant (DC 3225C) and 1.25% fragrance. Preferably homogenization is used when adding the DBS and HPC.

Example 22

The method of Example 19 may be used with the following changes: 34.3% propylene glycol, 17.5% silanol, 2.7% phenyltrimethicone, 40% Al Zr tetrchlorhydrex gly, 1.0% fragrance and 2.1% surfactant.

We claim:
1. A cosmetic composition made by combining in weight percent based on the total weight of the composition:
(a) from 5.0–50.0 percent of a silicone fluid phase comprising at least one hydroxy functionalized silicone fluid, at least one stabilizing agent and, optionally, at least one additional silicone material;
(b) from 40–95 percent of a gellant/solvent phase comprising a mixture of dibenzylidene sorbitol and at least one polyhydric alcohol solvent; and
(c) an effective amount of at least one active ingredient.
2. A cosmetic composition as claimed in claim 1 wherein at least one of the following ingredients is also added to the composition: emollient, fragrance, or coloring agent, and wherein each of the emollients, fragrances, or coloring agents may become part of either of the silicone phase or the gellant/solvent phase.
3. A cosmetic composition as claimed in claim 1 wherein the hydroxy functionalized silicone fluid is selected from the group consisting of
(a) a compound of Formula I:

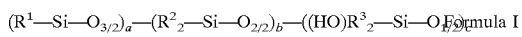

$$(R^1-Si-O_{3/2})_a-(R^2_2-Si-O_{2/2})_b-((HO)R^3_2-Si-O_{1/2})_c \quad \text{Formula I}$$

where each of $R^1$, $R^2$, and $R^3$, may be alike or different and are each independently selected from the group consisting of C1–C4 straight chain alkyls; a is a number in the range of 0–10; b is a number in the range of 0–10,000; c is a number in the range of 1–10; provided that a and b cannot both equal zero at the same time and a, b, and c are average values, including whole numbers and fractions; and
(b) mixtures of compounds of Formula I with the same or different values for a, b, c, $R^1$, $R^2$, and $R^3$.
4. A cosmetic composition as claimed in claim 3 wherein the R groups are each methyl.
5. A cosmetic composition as claimed in claim 3 wherein the hydroxy functionalized silicone fluid is selected from the group consisting of:
(a) linear polydimethylsiloxanediols where a=0, b=4–6,000;
(b) linear polydimethylsiloxanediols where a=0, b=4–1,000 and c=2;
(c) multifunctional branched siloxanes where a=1–2, b=0–1,000, and c=3–4;
(d) linear polydimethylsiloxanediols where a=0, b=40 and c=2;
(e) multifunctional branched siloxanes where a=1, b=16, and c=3;
(f) multifunctional branched siloxanes where a=1–2, b=10–1,000, and c=3–4;
(g) mixtures of the compounds listed in parts (a)–(f); and
(h) two component mixtures of the compounds listed in parts (a)–(f) wherein one component is 0.1–99.9% of the composition and the other component is the remainder to 100% based on weight.

6. A cosmetic composition as claimed in claim 5 wherein each of the R groups is methyl.

7. A cosmetic composition as claimed in claim 5 wherein for any of the groups (a)–(g), at least one additional silicone fluid is added in an amount of 0.1–90% hydroxy functionalized silicone and 10–99.9% of at least one silicone fluid based on weight.

8. A cosmetic composition as claimed in claim 7 wherein the at least one additional silicone fluid is selected from the group consisting of polydimethylsiloxanes, polydiethylsiloxanes, and polymethylethylsiloxanes, each having a viscosity from 350–2,500,000 centistoke.

9. A cosmetic composition as claimed in claim 3 wherein the hydroxy functionalized silicone fluid is selected from the group consisting of linear silanols of Formula IA:

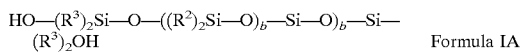
$$HO-(R^3)_2Si-O-((R^2)_2Si-O)_b-Si-O)_b-Si-(R^3)_2OH$$ Formula IA wherein $R^2$, $R^3$ and b have the same meanings as defined in claim 1.

10. A cosmetic composition as claimed in claim 3 wherein a has a value of 1–10.

11. A cosmetic composition as claimed in claim 10 wherein a has a value of 6–8.

12. A cosmetic composition as claimed in claim 3 wherein b has a value of 4–6000.

13. A cosmetic composition as claimed in claim 3 wherein c has a value of 2 or 3.

14. A cosmetic composition as claimed in claim 1 wherein the stabilizing agent is a member of the group consisting of silicone polyether surfactants having a hydrophilic/lipophilic balance compatible with the solvent and the silicone phase sufficient to form a stick composition.

15. A cosmetic composition as claimed in claim 1 wherein the stabilizing agent is a member of the group consisting of silicone polyether surfactants having a hydrophilic/lipophilic in the range of 1–10, and the solvent comprises greater than 50% by weight of propylene glycol, dipropylene glycol, tripropylene glycol, tetrapropylene glycol or mixtures of any of the foregoing.

16. A cosmetic composition as claimed in claim 14 wherein the stabilizing agent is a member of the group consisting of silicone polyether surfactants of Formula II:

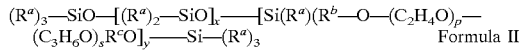
$$(R^a)_3-SiO-[(R^a)_2-SiO]_x-[Si(R^a)(R^b-O-(C_2H_4O)_p-(C_3H_6O)_sR^c O]_y-Si-(R^a)_3$$ Formula II wherein $R^a$ is an alkyl group of one to six carbon atoms; $R^b$ is $-C_mH_{2m}-$; $R^c$ is a terminating radical selected from the group consisting of hydrogen, an alkyl group of one to six carbon atoms, an ester group such as acyl, and phenyl; m is a number from two to eight; p and s are each selected so that segment $-(C_2H_4O)_p-(C_3H_6O)_s-$ has a molecular weight in the range of 200 to 5,000; x has a value of 8 to 400; and y has a value of 2 to 40.

17. A cosmetic composition as claimed in claim 16 in which for the polyether surfactants of Formula II, $R^a$ is a methyl group, $R^c$ is H; m is three or four, the group $R^b$ is $-(CH_2)_3-$; and the values of p and s are selected to provide a molecular weight of the segment $-(C_2H_4O)_p-(C_3H_6O)_s-$ of between 1,000 to 3,000.

18. A cosmetic composition as claimed in claim 14 wherein the stabilizing agent is a member of the group consisting of silicone polyether surfactants of Formula III:

$$(R^a)_3-SiO-[(R^a)_2-SiO]_x-[Si(R^a)(R^b-O-(C_2H_4O)_p-R^c)O]_y-Si-(R^a)_3$$ Formula III wherein $R^a$ is an alkyl group of one to six carbon atoms; $R^b$ is $-C_mH_{2m}-$; $R^c$ is a terminating radical selected from the group consisting of hydrogen, an alkyl group of one to six carbon atoms, an ester group, and phenyl; m is a number from two to eight; p is a number from 6 to 16; x is a number from 6 to 100; and y is a number from 1 to 20.

19. A cosmetic composition as claimed in claim 1 wherein the stabilizing agent is a member of the group consisting of a high refractive index modifier selected from the group consisting of isopropyl myristate, isopropyl palmitate, mineral oil, oleyl alcohol sorbitol, glycerol, octyl salicylate, octylmethoxycinnamate; phenyl siloxanes of Formula IV:

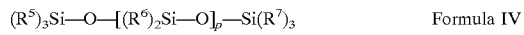
$$(R^5)_3Si-O-[(R^6)_2Si-O]_p-Si(R^7)_3$$ Formula IV where $R^5$, $R^6$ and $R^7$ are each independently selected from methyl and phenyl, and p is a number in the range of 0–10.

20. A cosmetic composition as claimed in claim 1 wherein the stabilizing agent is an alkyl galactomannose.

21. A cosmetic composition as claimed in claim 1 wherein the gellant/solvent phase is made by combining in weight percent based on the total weight of the cosmetic composition:

(a) 0.5–4.0 weight percent dibenzylidene sorbitol;

(b) 0.1–1.0 weight percent of a member of the group selected from the group consisting of hydroxypropyl cellulose, alkyl ester thickeners, fumed silica, waxes, hydroxy $C_3$–$C_4$ alkyl guars having a level of hydroxyalkylation of 0.4–1.5 molar substitution;

(c) 0.1–80 weight percent of a solvent selected from the group consisting of polyhydric alcohols, PPG-10 butane diol, 1.3-butane diol, PEG-6, PPG-425; and, optionally, up to 50 percent of the solvent portion comprising other solvents selected from propylene carbonate, diisopropyl sebacate, methyl pyrrolidone, and ethyl alcohol.

22. A cosmetic composition as claimed in claim 21 wherein in part (b) the waxes are alkyl methylsiloxanes.

23. A cosmetic composition as claimed in claim 21 wherein in part (c) the solvent is selected from the group consisting of propylene glycol, dipropylene glycol, tripropylene glycol, tetrapropylene glycol, PPG-10 butane diol, 1.3-butane diol, PEG-6, PPG-425 and mixtures thereof.

24. A cosmetic composition as claimed in claim 1 wherein the active ingredient is selected from the group consisting of antiperspirant salts, sunscreens, bacteriostats, fragrances and insect repellents.

25. A cosmetic composition as claimed in claim 24 wherein the active ingredient is selected from the group consisting of aluminum and aluminum/zirconium salts, and aluminum/zirconium salts complexed with a neutral amino acid.

26. A cosmetic composition as claimed in claim 1 wherein the active ingredient is selected from the group consisting of aluminum chlorohydroxide, aluminum chloride, aluminum sesquichlorohydroxide, zirconyl hydroxychloride, and aluminum chlorohydrolpropylene glycol complex.

27. A cosmetic composition as claimed in claim 1 wherein the active ingredient is selected from the group consisting of aluminum chlorohydrate, aluminum chloride, aluminum sesquichlorohydrate, zirconyl hydroxychloride, aluminum chlorohydrex PG, aluminum chlorohydrex PEG, aluminum dichlorohydrex PG, aluminum dichlorohydrex PEG, and aluminum-zirconium glycine complex wherein such aluminum-zirconium glycine complex is selected from the group consisting of aluminum zirconium trichlorohydrex gly, aluminum zirconium pentachlorohydrex gly, aluminum zirconium tetrachlorohydrex gly and aluminum zirconium octochlorohydrex gly.

28. A cosmetic composition as claimed in claim 1 wherein the active ingredient is selected from the group consisting of octyl methoxycinniamate, aminobenzoic acid, octyl salicylate, and oxybenzole.

29. A cosmetic composition as claimed in claim 1 wherein the active ingredient is selected from the group consisting of N,N-diethyl-m-toluamide and citronella.

30. A cosmetic composition as claimed in claim 1 wherein the active ingredient is selected from the group consisting of 2-amino-2-methyl-1-propanol, cetyltrimethylammonium bromide, cetyl pyridinium chloride, 2,4,4'-trichloro-2'-hydroxydiphenylether, N-(4-chlorophenyl)-N'-(3,4-dichlorophenyl)urea and zinc ricinoleate.

31. A cosmetic composition as claimed in any one of claims 24, 25, 26 or 27 further comprising the addition of 0.5%–1.0% guanidine carbonate.

32. A cosmetic composition as claimed in claim 1 wherein the composition comprises in percent by weight based on the total weight of the composition:

(a) 6.0–35% of the silicone fluid phase;

(b) 25–7% of a polyhydric alcohol selected from the group consisting of propylene glycol, dipropylene glycol, tripropylene glycol, tetrapropylene glycol and mixtures thereof;

(c) 1.5–2.5% dibenzylidene sorbitol; and (d) 5–25% antiperspirant active.

33. A cosmetic composition for reducing body malodor comprising a composition as claimed in any one of claims 1–30 or 32.

* * * * *

UNITED STATES PATENT AND TRADEMARK OFFICE
CERTIFICATE OF CORRECTION

PATENT NO.: 5,871,720

DATED: February 16, 1999

INVENTOR(S): Adriana Urrutia Gutierrez; Joseph James Albanese; Robert Joseph Bianchini; Steven Louis Fantano It is certified that error appears in the above-identified patent and that said Letters Patent is hereby corrected as shown below:

On the title page, Item [73] Assignee should read --

Colgate-Palmolive Company
New York, New York; and

Dow Corning Corporation
Midland, Michigan --

Attorney, Agent, or Firm
Patent Attorneys on front of patent should read:
    Rosemary M. Miano
    James DeCesaré

Signed and Sealed this

Twenty-fifth Day of May, 1999

Attest:

Q. TODD DICKINSON

*Attesting Officer*     Acting Commissioner of Patents and Trademarks

UNITED STATES PATENT AND TRADEMARK OFFICE
CERTIFICATE OF CORRECTION

PATENT NO. : 5,871,720

DATED : February 16, 1999

INVENTOR(S) : Adriana Urrutia-Gutierrez; Joseph James Albanese; Robert Joseph Bianchini; Steven Louis Fantano It is certified that error appears in the above-identified patent and that said Letters Patent is hereby corrected as shown below:

The name of the First Inventor should read:

Adriana Urrutia-Gutierrez

Signed and Sealed this

Twenty-fourth Day of August, 1999

Attest:

Q. TODD DICKINSON

Attesting Officer     Acting Commissioner of Patents and Trademarks